United States Patent [19]

Karrer

[11] Patent Number: 4,563,894

[45] Date of Patent: Jan. 14, 1986

[54] PARAMAGNETIC OXYGEN SENSOR

[75] Inventor: Henry E. Karrer, Palo Alto, Calif.

[73] Assignee: Hewlett-Packard Company, Palo Alto, Calif.

[21] Appl. No.: 642,972

[22] Filed: Aug. 21, 1984

[51] Int. Cl.⁴ ............ G01N 29/02; G01R 33/12; G01F 1/66

[52] U.S. Cl. ............ 73/24; 73/27 A; 73/861.27

[58] Field of Search ............ 73/24, 27 A, 23, 643, 73/861.27; 324/204

[56] References Cited

U.S. PATENT DOCUMENTS

| | | | |
|---|---|---|---|
| 2,416,344 | 2/1947 | Pauling | 73/27 A |
| 3,584,499 | 6/1971 | Hummel | 73/23 |
| 3,616,679 | 11/1971 | Meyer et al. | 73/27 A |
| 4,173,975 | 11/1979 | DeLong et al. | 73/27 A |
| 4,403,186 | 9/1983 | Kotani et al. | 73/27 A |
| 4,480,483 | 11/1984 | McShane | 73/861.27 |

Primary Examiner—Stephen A. Kreitman
Attorney, Agent, or Firm—Leslie G. Murray

[57] ABSTRACT

Apparatus comprising a test chamber, an electric solenoid and a pressure detector is provided to measure the partial pressure of oxygen contained in a mixture of gases. As a result of the paramagnetic properties of oxygen, an acoustic wave is produced in the gas mixture by the application of a pulsed magnetic field. The magnitude of the dynamic acoustic wave is dependent on the amount of oxygen present in the gas mixture. The solenoid generates a pulsating magnetic field in response to an electric signal provided by a signal source. The pressure detector measures the magnitude of the resulting acoustic wave and provides a signal whose amplitude is directly proportional to the amount of oxygen present in the sample gas.

11 Claims, 3 Drawing Figures

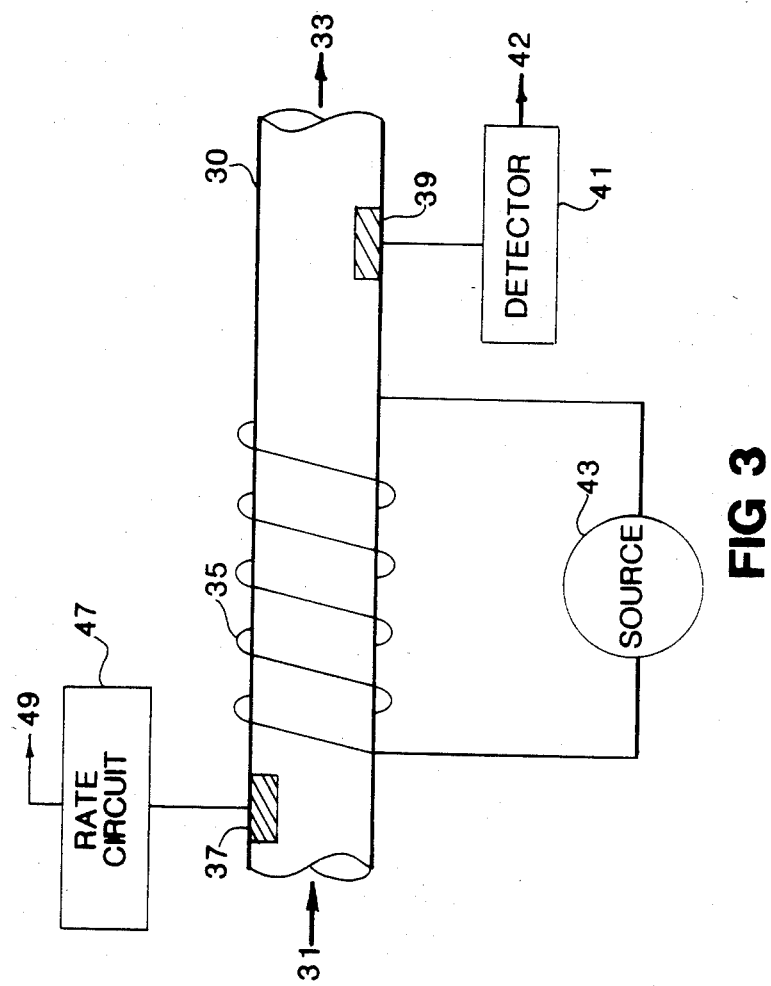

PARAMAGNETIC OXYGEN SENSOR

BACKGROUND OF THE INVENTION

The present invention relates in general to the measurement of the partial pressure of a particular gas in a mixture of gases, and more particularly, to an instrument for measuring respiratory oxygen content which utilizes the paramagnetic properties of oxygen to generate an acoustic wave in the gas mixture by the rapid application of a magnetic field.

Techniques utilizing the paramagnetic properties of a gas, such as oxygen, to measure partial pressure of the gas in a mixture of gases are well known in the prior art. Oxygen is unique in that it is about 100 times more susceptible to magnetism than are the other respiratory gases. In the presence of a magnetic field, oxygen undergoes apparent changes in density, viscosity and thermal conductivity attributable to its paramagnetism. These changes may be modulated by changes in the temperature and magnetic field. All of these effects have been previously employed in instruments to measure the partial pressure of oxygen present in respiratory gases.

One type of apparatus is disclosed in U.S. Pat. No. 2,416,344 issued on Feb. 25, 1947, to Linus Pauling. Such apparatus is based on the principle that the force acting on a test body in an inhomogeneous magnetic field is dependent on the magnetic susceptibility of the gas surrounding the test body. Apparatus of the type described in U.S. Pat. No. 2,416,344 utilizes two glass spheres filled with nitrogen fixed at opposite ends of a horizontal bar suspended on quartz fiber placed in an inhomogeneous magnetic field. Any oxygen admitted to the apparatus will concentrate between the poles of the magnet and due to its relatively high density will displace the nitrogen filled spheres. The force displacing the spheres is proportional to the concentration of the oxygen present and is balanced by the suspension fiber torque. The angular deflection of the spheres is proportional to the concentration of oxygen present.

A paramagnetic gas analyzer of the "magnetic wind" type, which utilizes the principle that the magnetic susceptibility of oxygen varies inversely with its temperature, is disclosed by U.S. Pat. No. 3,616,679, issued to Emilio G. Meyer and Gianmario Bardoni on Nov. 2, 1971. The apparatus of U.S. Pat. No. 3,616,679 heats the sample of gas in an inhomogeneous magnetic field inside a cylindrical test chamber. When the sample gas includes a paramagnetic gas, such as oxygen, a magnetic wind will be generated in the direction of decreasing magnetic field intensity adjacent the heating elements. This wind flows over separate temperature responsive sensors, and the resulting change in temperature of the sensors is measured by a suitable electrical circuit. The output from the measurement circuit is a voltage proportional to the concentration of the paramagnetic gas present in the sample supplied to the apparatus.

U.S. Pat No. 4,173,975, issued to Daniel L. Delong and Edward L. Rich on Nov. 13, 1979, discloses an apparatus wherein a reference chamber is oscillated into and out of an air gap of a magnetic circuit by means of a piezoelectric bender bar. The magnetic circuit is immersed in an ambient gas mixture containing oxygen to be measured, and a background gas. This ambient gas fills the gap area resulting in a certain magnetic flux in the magnetic circuit. The movement of the reference chamber into and out of the gap will vary the magnetic flux, the amount of variation being indicative of the partial pressure of the oxygen present in the ambient gas mixture. A flux change sensing means is provided to measure the change in the magnetic flux in the magnetic circuit due to the reference chamber oscillating into and out of the gap.

U.S. Pat. No. 3,584,499, entitled Quick Response Oxygen Analyzer, issued to Heinz Hummel on June 15, 1971, discloses an apparatus which utilizes a pressure difference detector to measure the difference of alternating pressure of a sample gas and a comparison or reference gas in an alternating inhomogeneous magnetic field. The magnetic susceptibilities of the two gases depend proportionately on the oxygen content of the two gases. It can be demonstrated that the difference of alternating pressure is proportional to the susceptibility difference between the sample gas and the reference gas. Hence, if the oxygen content and the magnetic susceptibility of the reference gas is known, the oxygen content of the sample gas can be determined.

Apparatus measuring the oxygen uptake of a person breathing 100 percent oxygen on a breath by breath basis must meet exacting performance requirements. Normal oxygen uptake is on the order of several percent, and variations in the oxygen uptake of ten to twenty percent are significant. The mearsurement of oxygen uptake for a person receiving 100 percent oxygen therefore requires an accuracy on the order of 0.1 percent. Further, to make this measurement utilizing simultaneous measurement of flow and integration of the product of flow and oxygen concentration requires response time on the order of 0.050 seconds.

The thermomagnetic methods, as well as those dependent on diffusion about a heated filament, relying on sluggishness of molecules have a response time of about 0.1 second. Analyzers employing the Pauling principle cannot meet this quick response requirement because of high volume requirements and limited flow rates. Instruments utilizing thermomagnetic effects to cool a heated filament, magnetic wind, are influenced by the carrier gas and are quite delicate of construction and require much adjustment. Analyzers operating on the Pauling principle are also affected by the carrier gas. Further, almost all of the above-mentioned instruments require unusual types of magnetic pole pieces.

SUMMARY OF THE INVENTION

Prior art paramagnetic methods utilize some measure of the steady state effect produced by a magnetic field on a gas mixture. The application of a magnetic field causes the magnetic dipoles of the gas molecules to experience a torque tending to align the dipoles with the applied magnetic field. In the case of oxygen, unpaired electron spins tend to align with the applied field. Very quickly, the population of dipole alignments shifts slightly in favor of alignment with the applied field. The force of each dipole is proportional to the local field gradient. The oxygen molecules are drawn towards the regions of greatest field strength and molecules of diamagnetic gases are pushed from these regions. The action of the magnetic field accelerating the oxygen molecules towards the regions of greatest field strength generates an acoustic wave. If the magnetic field is maintained, the acoustic disturbance will propogate throughout the medium, be dissipated, and an equilibrium condition established. Measurements made after the acoustic wave has dissipated are static or steady state measurements. The present invention measures the magnitude of the acoustic wave itself to determine the oxygen content of the gas mixture.

The present invention provides a test chamber having input and exit ports, a solenoid and a pressure detector. The solenoid generates a pulsating magnetic field in response to an electrical signal provided by an electrical source. The pressure detector or microphone measures the magnitude of the resulting acoustic wave and provides a signal whose amplitude is proportional to the amount of oxygen present in the sample gas.

The invention has several unique advantages over the prior art. Firstly, since this is an AC detection scheme, special detection methods may be utilized to increase the signal to noise ratio. For example, if the electric source provides a CW signal, then synchronous detection may be used; if the source provides a pulsed signal, then a matched filter detector may be used. Secondly, the concentration of oxygen in a sample gas flowing in a conduit can be noninvasively measured. Thirdly, the sensor does not consume oxygen as do many other types of existing oxygen sensors. Fourthly, the acoustic wave produced by a solenoid disposed adjacent to a conduit may be utilized to measure the velocity or the flow rate of the sample gas in the conduit. Finally, the response time is limited only by the speed of sound in gas being measured.

DESCRIPTION OF THE DRAWINGS

FIG. 3 is a diagram illustrating another embodiment of the invention.

DESCRIPTION OF THE PREFERRED EMBODIMENT

Figure 1:
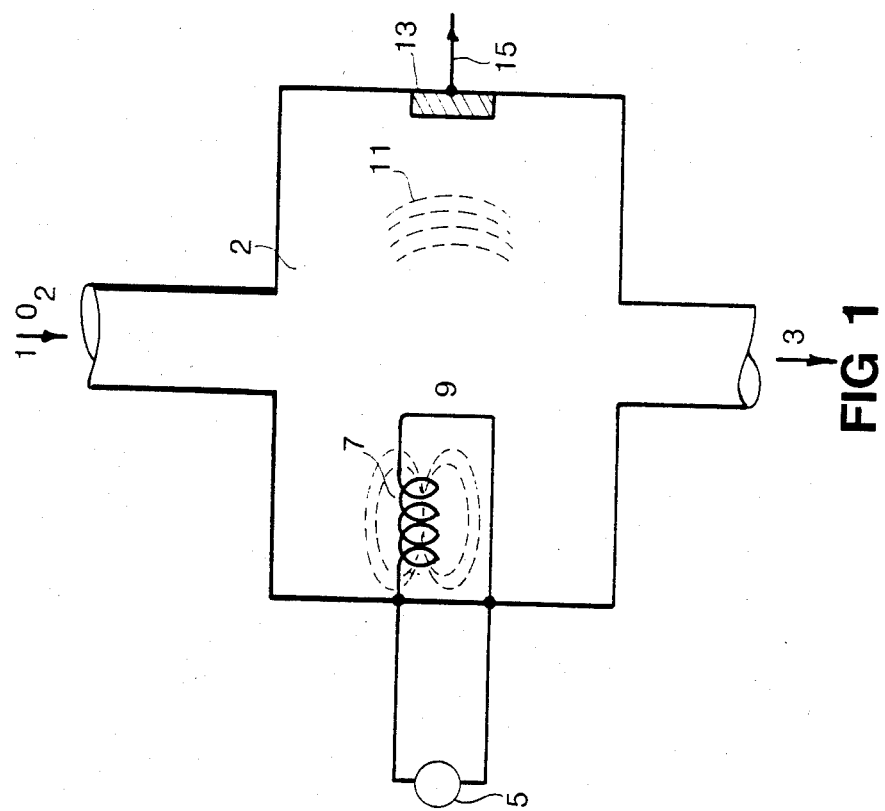
FIG. 1 is a diagram illustrating the preferred embodiment of the invention.

Referring now to FIG. 1, a sample gas comprising a mixture of gases, including oxygen, enters the test chamber 2 at the inlet port 1 and exits at the outlet port 3. A solenoid 7 is driven by a CW or pulsed source 5. The solenoid 7 can be disposed either inside or outside of the test chamber 2. The source 5 provides an electrical signal ($F_{in}$) with a frequency, $f_o$, in the range 1 KHz to 10 MHz. The solenoid in response to $F_{in}$ generates a pulsating magnetic field at this same frequency, $f_o$. Any oxygen present in the sample gas will be drawn towards the region 9 of the magnetic field where the field gradient is strongest. Non-magnetic gases present in the sample gas will be unaffected by the magnetic field. The effect of the magnetic field upon the sample gas is to create a local pressure disturbance when any oxygen present is drawn towards the region 9 and to generate a sound or acoustic wave 11 at frequency $f_o$. The acoustic wave 11 will propagate from region 9 to a microphone or acoustic detector 13. The detector 13 will output a signal on line 15 whose amplitude will be proportional to the magnitude of the acoustic wave 11 and hence indicative of the concentration of oxygen present in the sample gas. If no oxygen were present in the sample gas, no acoustic wave would be generated.

Figure 2:
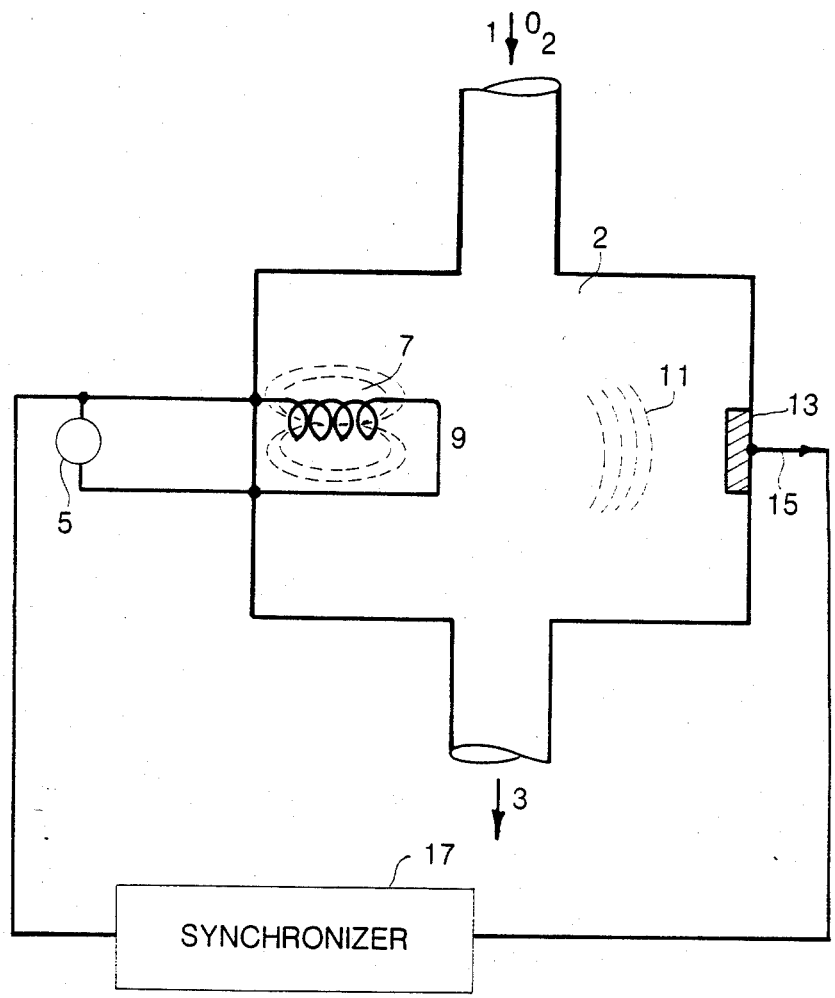
FIG. 2 is a diagram illustrating a modification to the preferred embodiment of the invention.

Referring now to FIG. 2, the apparatus of FIG. 1 has been modified to include a synchronizing circuit 17 which gates the detector 13 at the CW frequency $f_o$, and synchronizes the detector 13 with the CW source 5. This modification provides a very narrow band output signal from the detector 13 and greatly improves the signal to noise ratio. Similarly, if the source 5 is singly pulsed, the detector 13 can be gated to detect the acoustic pulse only at a specific time; if the source 5 provides a pulse train, a corresponding matched filter may be utilized.

FIG. 3 illustrates another embodiment of the invention which provides the capability to non-invasively measure oxygen concentration in a gas flowing in a pipe or conduit 30. A coil 35 is mounted axially on the pipe section 30 and the sample gas mixture enters at 31 and flows through the core section of coil 35 exiting at 33. A CW or pulsed source 43 provides an electrical signal, $F_{in}$, having a frequency, $f_o$, which is applied to the coil 35 generating a pulsating magnetic field at frequency $f_o$. The effect of the magnetic field on the oxygen present in the sample gas will generate an acoustic wave which propagates down the pipe 30. A microphone or pressure detector 39, downstream of the solenoid 35, detects the passage of the pressure disturbance and outputs a signal to the detector circuit 41. The amplitude of the detector circuit 41 output signal on line 42 is proportional to the amount of oxygen present in the sample gas. An additional detector 37 may be added on the upstream side of the solenoid 35. When the solenoid 35 is pulsed, an acoustic wave is generated in the sample gas at each end of the solenoid 35. The acoustic waves will generate equal amplitude signals at the detectors 37 and 39 if the detectors are equidistant from the solenoid 35. However, the acoustic waves will arrive at the respective detectors at different times since one wave is propagating through the gas in the direction of flow of the gas, and the other wave is propagating opposite to the direction of gas flow. This time difference may be used in the rate circuit 47 to provide an output signal on line 49 proportional to the velocity or flow rate of the sample gas in the conduit.

A solenoid is not the only possible source of the magnetic field, the only requirement is that the magnetic field have a high gradient. It will be understood by those skilled in the art that various changes and omissions in the form and detail thereof as indicated, may be therein without departing from the spirit and scope of the invention.

I claim:

1. Apparatus for measuring the concentration of a paramagnetic gas in a gaseous mixture, said apparatus comprising:
    a test chamber;
    gas inlet and outlet means coupled to the test chamber for introducing the gaseous mixture into the test chamber;
    first means for generating a periodically excited magnetic field, said first means disposed within the test chamber for providing a region of high magnetic field intensity gradient, said paramagnetic gas responsive to said magnetic field and accelerated towards said region of high magnetic field intensity gradient thereby generating an acoustic wave, the acoustic wave propagating throughout the gaseous mixture within the test chamber; and
    detector means disposed on the side wall of said test chamber for detecting said acoustic wave and providing an output signal, the amplitude of said output signal indicative of the concentration of said paramagnetic gas in the gaseous mixture.

2. Apparatus as in claim 1 wherein said first means for generating a periodically excited magnetic field comprises:

a solenoid, responsive to an electric signal, for generating said periodically excited magnetic field at a predetermined frequency; and second means coupled to said solenoid for providing said electrical signal at said predetermined frequency.

3. Apparatus as in claim 2 wherein said second means comprises a continuous wave signal source for providing said electric signal at said predetermined frequency.

4. Apparatus as in claim 2 wherein said detector means comprises:

gating means to gate said detector means at said predetermined frequency; and third means to synchronize said gating means with said second means.

5. Apparatus for measuring the concentration of paramagnetic gas in a gaseous mixture, said apparatus comprising:

a conduit for the flow of the gaseous mixture;

first means generating a periodically excited magnetic field at a predetermined frequency, said first means disposed closely adjacent to the conduit, for providing a region of high magnetic field intensity gradient within the conduit, said paramagnetic gas responsive to said magnetic field and accelerated towards said region of high magnetic field intensity gradient thereby generating an acoustic wave, the acoustic wave propagating longitudinally along the conduit in the gaseous mixture; and detector means disposed on the side wall of said conduit for detecting said acoustic wave and providing an output signal, the amplitude of said output signal indicative of the concentration of said paramagnetic gas in the gaseous mixture.

6. Apparatus as in claim 5 wherein said first means for generating a periodically excited magnetic field at a predetermined frequency comprises:

a solenoid disposed around said conduit, responsive to an electric signal for generating said periodically excited magnetic field at said predetermined frequency; and second means coupled to said solenoid for providing said electric signal at said predetermined frequency.

7. Apparatus as in claim 6 wherein said second means comprises a continuous wave signal source for providing said electric signal at said predetermined frequency.

8. Apparatus as in claim 6 wherein said detector means comprises:

gating means to gate said detector means at said predetermined frequency; and third means to synchronize said gating means with said second means.

9. Apparatus as in claim 6 wherein said detector means comprises a pair of pressure detectors disposed on he side wall of said conduit on opposite sides of and equidistant from said solenoid for detecting said acoustic wave and providing a pair of first output signals.

10. Apparatus as in claim 6 wherein said detector means further comprises:

first circuit means for comparing the arrival times of said acoustic wave at said pair of pressure detectors respectively and determining the time difference therebetween; and second circuit means responsive to said time difference for providing a second output signal indicative of the flow rate of the gaseous mixture.

11. Apparatus as in claim 10 further comprising:

gating means for gating said detector means at said predetermined frequency; and third means to synchronize said gating means with said second means.

* * * * *